United States Patent
Gilhooley et al.

(10) Patent No.: US 12,279,779 B2
(45) Date of Patent: Apr. 22, 2025

(54) SURGICAL DRILLING SYSTEM FOR DETERMINING BONE BREAKTHROUGH

(71) Applicant: Stryker European Operations Limited, Carrigtwohill (IE)

(72) Inventors: Séamus Gilhooley, Athenry (IE); Yuk Lam Krista Lee, Strabane (IE); Eugene O'Keeffe, Kilworth (IE); Rok Kordez, Ljubljana (SI)

(73) Assignee: Stryker European Operations Limited, Carrigtwohill (IE)

( * ) Notice: Subject to any disclaimer, the term of this patent is extended or adjusted under 35 U.S.C. 154(b) by 373 days.

(21) Appl. No.: 17/917,985

(22) PCT Filed: Apr. 9, 2021

(86) PCT No.: PCT/IB2021/052965
§ 371 (c)(1),
(2) Date: Oct. 10, 2022

(87) PCT Pub. No.: WO2021/205397
PCT Pub. Date: Oct. 14, 2021

(65) Prior Publication Data
US 2023/0144537 A1 May 11, 2023

Related U.S. Application Data

(60) Provisional application No. 63/008,060, filed on Apr. 10, 2020.

(51) Int. Cl.
*A61B 17/16* (2006.01)
*A61B 34/30* (2016.01)
(Continued)

(52) U.S. Cl.
CPC ........ *A61B 17/1615* (2013.01); *A61B 17/162* (2013.01); *A61B 17/1626* (2013.01);
(Continued)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS

| 5,575,650 | A  | * | 11/1996 | Niznick | ............. A61B 17/1615 |
| | | | | | 433/165 |
| 6,665,948 | B1 | * | 12/2003 | Kozin   | .................... A61B 90/06 |
| | | | | | 175/45 |

(Continued)

FOREIGN PATENT DOCUMENTS

| CN | 116801822 A | * | 9/2023 | ......... A61B 17/1626 |
| EP | 4132384 B1 | * | 4/2024 | ......... A61B 17/1615 |

(Continued)

OTHER PUBLICATIONS

International Search Report for Application No. PCT/IB2021/052965 dated Jul. 1, 2021, 3 pages.

*Primary Examiner* — Eric S Gibson
(74) *Attorney, Agent, or Firm* — Howard & Howard Attorneys PLLC (57) ABSTRACT

A surgical drill bit for bone drilling and for determining a characteristic of a drilling medium from a characteristic of fluid flow. The surgical drill bit includes a shank portion for coupling to a drill chuck. The shank portion defines a proximal opening. The surgical drill bit also includes a drilling portion for drilling through bone. A distal cutting region (62) of the drilling portion includes a rake surface (66), a clearance surface (68), and a flank surface (70). The flank surface (70) defines a distal opening (72) and is configured to abut the bone such that the distal opening is occluded by the bone while the rake surface is cutting into the bone. The shank and drilling portions collectively define an inner channel in fluid communication with the proximal (Continued)

and distal openings. The distal opening is occluded by the bone during drilling to establish fluid pressure within the inner channel.

17 Claims, 7 Drawing Sheets

(51) Int. Cl.
    *B25J 9/16*              (2006.01)
    *A61B 17/00*           (2006.01)
    *A61B 90/00*           (2016.01)
    *B25J 13/08*            (2006.01)

(52) U.S. Cl.
    CPC .......... *A61B 17/1628* (2013.01); *A61B 34/30* (2016.02); *B25J 9/1628* (2013.01); *A61B 2017/00022* (2013.01); *A61B 2090/031* (2016.02); *B25J 13/088* (2013.01)

(58) Field of Classification Search
    CPC ............ A61B 17/1622; A61B 17/1624; A61B 17/1626; A61B 17/1628; A61B 17/1631; A61B 17/164; A61B 17/1644; A61B 17/1646; A61B 17/1655; A61B 17/1657; A61B 17/1671; A61B 2017/00022; A61B 2017/00123; A61B 2017/1648; A61B 2017/1651; A61B 2017/1653; A61B 34/30; B25J 13/08; B25J 13/088; B25J 13/089
See application file for complete search history.

(56) References Cited

U.S. PATENT DOCUMENTS

| | | | |
|---|---|---|---|
| 8,894,654 B2 * | 11/2014 | Anderson | B25B 21/002 |
| | | | 173/176 |
| 9,204,885 B2 * | 12/2015 | McGinley | A61B 17/162 |
| 9,826,984 B2 * | 11/2017 | McGinley | A61B 17/142 |
| 10,149,686 B2 * | 12/2018 | Anderson | A61B 17/1626 |
| 10,195,007 B2 * | 2/2019 | Ahmadi | A61C 1/055 |
| 11,317,927 B2 * | 5/2022 | Carusillo | A61B 17/1631 |
| 11,517,326 B1 * | 12/2022 | Sharma | A61B 17/1615 |
| 11,564,700 B2 * | 1/2023 | Detinis | A61B 17/1628 |
| 11,857,204 B2 * | 1/2024 | Windolf | A61B 90/06 |
| 11,896,239 B2 * | 2/2024 | Carusillo | A61B 17/1637 |
| 12,089,856 B2 * | 9/2024 | Detinis | A61B 34/30 |
| 2009/0220563 A1 | 9/2009 | Shachar | |
| 2010/0081111 A1 * | 4/2010 | Better | A61C 19/06 |
| | | | 433/215 |
| 2017/0119421 A1 * | 5/2017 | Staunton | F16J 15/3256 |
| 2017/0202637 A1 * | 7/2017 | Ahmadi | A61B 5/746 |
| 2019/0262031 A1 | 8/2019 | Efremkin | |
| 2022/0240951 A1 * | 8/2022 | Detinis | A61B 17/1628 |
| 2023/0144537 A1 * | 5/2023 | Gilhooley | A61B 90/06 |
| | | | 606/80 |
| 2023/0172619 A1 * | 6/2023 | Detinis | A61B 17/1628 |
| | | | 606/80 |

FOREIGN PATENT DOCUMENTS

| | | | | |
|---|---|---|---|---|
| WO | 0209598 A2 | 2/2002 | | |
| WO | 2011131357 A2 | 10/2011 | | |
| WO | 2018183002 A1 | 10/2018 | | |
| WO | 2019040381 A1 | 2/2019 | | |
| WO | WO-2021205397 A1 * | 10/2021 | ......... | A61B 17/1615 |
| WO | WO-2022162674 A1 * | 8/2022 | ......... | A61B 17/1626 |

* cited by examiner

FIG. 12

SURGICAL DRILLING SYSTEM FOR DETERMINING BONE BREAKTHROUGH

RELATED APPLICATIONS

The subject patent application claims priority to and all the benefits of U.S. Provisional Patent Application No. 63/008,060, filed on Apr. 10, 2020, which is hereby incorporated herein by reference in its entirety.

BACKGROUND

Conventional medical and surgical procedures routinely involve the use of surgical tools and instruments which allow surgeons to approach and manipulate surgical sites. By way of non-limiting example, rotary instruments such as handheld drills are commonly utilized in connection with orthopedic procedures to address various musculoskeletal conditions, such as trauma, sports injuries, degenerative diseases, joint reconstruction, and the like. In procedures where handheld drills or similar surgical instruments are employed, rotational torque selectively generated by an actuator (e.g., an electric motor) is used to rotate a releasably-attachable drill bit or other surgical attachments at different speeds. The drill bit may commonly be used to create bore holes for many different purposes, such as to place screws to repair a bone fracture trauma with to hold a fixator in place.

While handheld surgical instruments and drill bits are routinely utilized to assist in the performance of a variety of different types of medical and/or surgical procedures, there is a need in the art to continuously improve such drill bits and handheld surgical instruments.

SUMMARY

The present disclosure relates generally to a surgical drilling system configured for bone drilling. The surgical drilling system is also configured to determine a characteristic of a drilling medium from a characteristic of fluid flow. The surgical drilling system includes a drill chuck configured to be rotated by a motor. The surgical drilling system also includes a surgical drill bit configured to be coupled to the drill chuck. The surgical drill bit includes a shank portion extending distally along a drill bit axis from a proximal end. The shank portion is configured to be coupled to and rotated by the drill chuck. The shank portion has a proximal surface defining a proximal opening. The surgical drill bit also includes a drilling portion for drilling through bone. The drilling portion extends distally along the drill bit axis from the shank portion to a distal end. The drilling portion has a distal cutting region. The distal cutting region includes a rake surface for cutting into a bone while drilling. The distal cutting region also includes a clearance surface for directing bone chips away from the bone during drilling. The distal cutting region also includes a flank surface disposed between the rake surface and the clearance surface. The flank surface defines a distal opening. The flank surface is configured to abut the bone such that the distal opening is occluded by the bone while the rake surface is cutting into the bone. The shank and drilling portions collectively define an inner channel in fluid communication with the proximal and distal openings. The distal opening is configured to be occluded by the bone during drilling to establish fluid pressure within the inner channel. The surgical drilling system also includes a pump configured to transfer fluid from a fluid source into the inner channel of the surgical drill bit through the proximal opening of the surgical drill bit. The surgical drilling system also includes a sensor disposed in fluid communication with the inner channel and configured to generate a signal responsive to a characteristic of the fluid being transferred to the inner channel of the surgical drill bit. The surgical drilling system also includes a controller configured to receive the signal from the sensor and determine a characteristic of the drilling medium at the distal opening of the surgical drill bit based on the signal.

Another exemplary configuration provides a surgical drilling system configured for bone drilling. The surgical drilling system is also configured to determine a characteristic of a drilling medium from a characteristic of fluid flow. The surgical drilling system includes a drill chuck configured to be rotated by a motor. The surgical drilling system also includes a surgical drill bit configured to be coupled to the drill chuck. The surgical drill bit includes a shank portion extending distally along a drill bit axis from a proximal end. The shank portion is configured to be coupled to and rotated by the drill chuck. The shank portion has a proximal surface defining a proximal opening. The surgical drill bit also includes a drilling portion for drilling through bone. The drilling portion extends distally along the drill bit axis from the shank portion to a distal end. The drilling portion has a distal cutting region. The distal cutting region includes a rake surface for cutting into a bone while drilling. The distal cutting region also includes a clearance surface for directing bone chips away from the bone during drilling. The distal cutting region also includes a flank surface disposed between the rake surface and the clearance surface. The flank surface defines a distal opening. The flank surface is configured to abut the bone such that the distal opening is occluded by the bone while the rake surface is cutting into the bone. The shank and drilling portions collectively define an inner channel in fluid communication with the proximal and distal openings. The distal opening is configured to be occluded by the bone during drilling to establish fluid pressure within the inner channel. The surgical drilling system also includes a pump configured to transfer fluid from a fluid source into the inner channel of the surgical drill bit through the proximal opening of the surgical drill bit. The surgical drilling system also includes a sensor disposed in fluid communication with the inner channel and configured to generate a signal responsive to a characteristic of the fluid being transferred to the inner channel of the surgical drill bit. The surgical drilling system also includes a controller configured to receive the signal from the sensor and determine a characteristic of the drilling medium at the distal opening of the surgical drill bit based on the signal.

Yet another exemplary configuration provides a surgical drilling system configured for bone drilling. The surgical drilling system is also configured to determine a characteristic of a drilling medium from a characteristic of fluid flow. The surgical drilling system includes a drill chuck configured to be rotated by a motor. The surgical drilling system also includes a surgical drill bit extending from a proximal end to a distal end along a drill bit axis. The surgical drill bit is configured to be coupled to the drill chuck and configured to rotate with the drill chuck. The surgical drill bit includes a shank portion adjacent the proximal end of the surgical drill bit. The shank portion is configured to be coupled to and rotated by the drill chuck. The shank portion has a proximal surface defining a proximal opening. The surgical drill bit also includes a drilling portion for drilling through bone. The drilling portion extends distally along the drill bit axis from the shank portion to the distal end of the surgical drill bit. The drilling portion includes a distal cutting region adjacent the distal end of the surgical drill bit for plunging into the bone. The drilling portion also includes a fluted region disposed between the shank portion and the distal cutting region. The fluted region includes a lateral surface defining a lateral opening. The shank and drilling portions collectively define an inner channel in fluid communication with the proximal and lateral openings. The lateral opening is configured to be occluded by the bone during drilling to establish fluid pressure within the inner channel. The surgical drilling system also includes a pump configured to transfer fluid from a fluid source into the inner channel of the surgical drill bit through the proximal opening of the surgical drill bit. The surgical drilling system also includes a sensor disposed in fluid communication with the inner channel and configured to generate a signal responsive to a characteristic of the fluid being transferred to the inner channel of the surgical drill bit. The surgical drilling system also includes a controller configured to receive the signal from the sensor and determine a characteristic of the drilling medium at the lateral opening of the surgical drill bit based on the signal.

Another exemplary configuration provides a surgical drilling system configured for bone drilling. The surgical drilling system is also configured to determine a characteristic of a drilling medium from a characteristic of fluid flow. The surgical drilling system includes a drill chuck configured to be rotated by a motor. The surgical drilling system also includes a surgical drill bit for drilling through bone. The surgical drill bit is configured to be coupled to the drill chuck and configured to rotate with the drill chuck. The surgical drill bit extends distally along a drill bit axis from a proximal end to a distal end. The surgical drill bit defines a first inner channel extending distally from the proximal end. The first inner channel has a first geometrical configuration. The first inner channel has a first outlet configured to be occluded during drilling to establish fluid pressure within the first inner channel. The surgical drill bit also includes a second inner channel extending distally from the proximal end. The second inner channel has a second geometrical configuration different from the first geometrical configuration. The second inner channel has a second outlet configured to be occluded during drilling to establish fluid pressure within the second inner channel. The surgical drilling system also includes a pump configured to transfer fluid from a fluid source into the first and second inner channels of the surgical drill bit. The system also includes a sensor disposed in fluid communication with the first and second inner channels. The sensor is configured to generate a first signal responsive to a first characteristic of the fluid being transferred to the first inner channel of the surgical drill bit corresponding to occlusion of the first outlet. The sensor is configured to generate a second signal different from the first signal responsive to a second characteristic of the fluid being transferred to the second inner channel of the surgical drill bit corresponding to occlusion of the second outlet. The surgical drilling system also includes a controller configured to receive the first and second signals from the sensor and determine a characteristic of the drilling medium at the first and second outlets based on the first and second signals.

DETAILED DESCRIPTION

Figure 1:
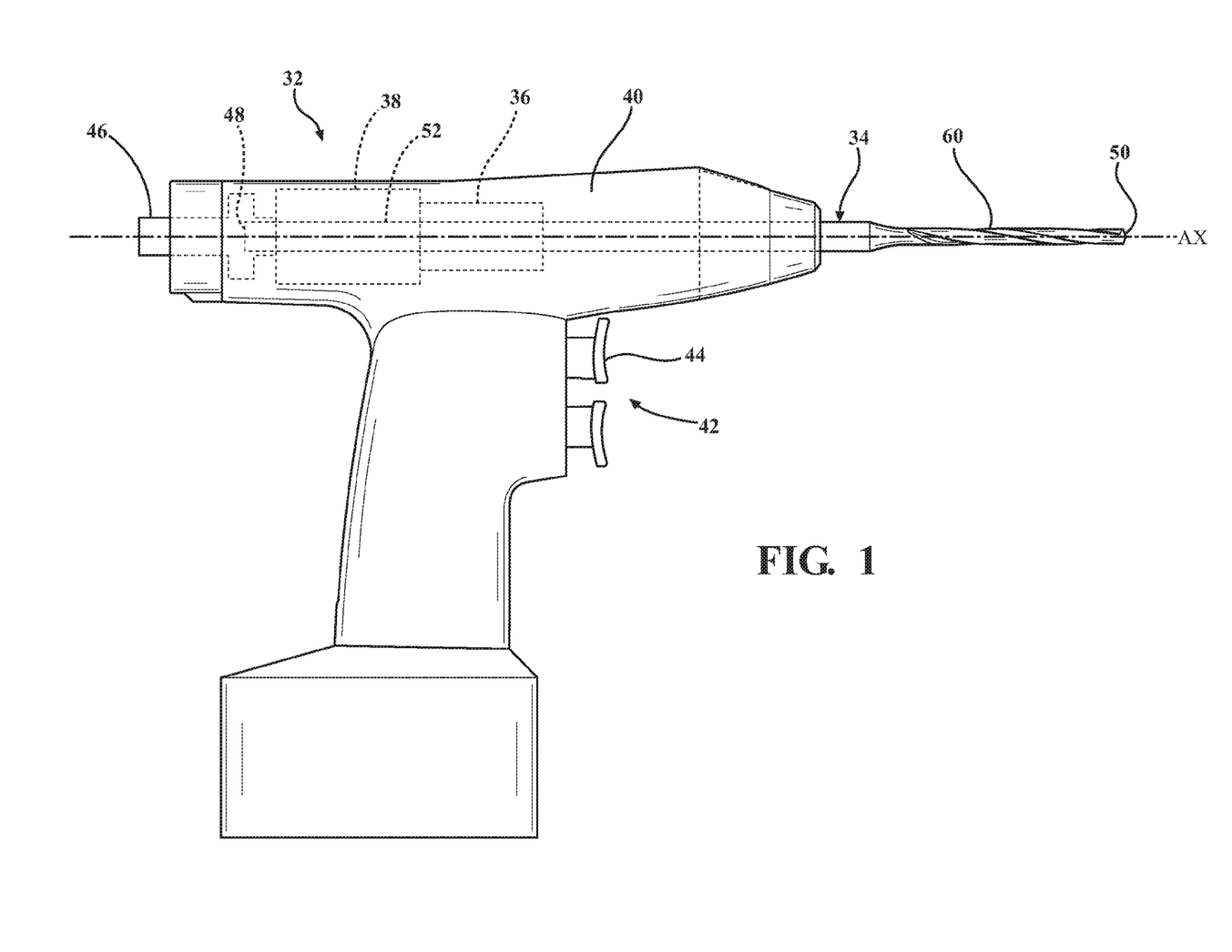
FIG. 1 is a perspective view of a surgical drill assembly and a surgical drill bit of a surgical drilling system.

FIG. 1 depicts a perspective view of a surgical drill assembly 32 and a surgical drill bit 34 of a surgical drilling system 30. The surgical drilling system 30 may be configured for bone drilling. The surgical drill assembly 32 may include a drill chuck 36 and a motor 38 disposed within a housing 40. The drill chuck 36 is operatively coupled to the motor 38 such that the motor 38 is configured to rotate the drill chuck 36. The drill chuck 36 is configured to secure the surgical drill bit 34 to the surgical drill assembly 32. The motor 38 is configured to rotate the drill chuck 36 and the surgical drill bit 34 in unison. It is contemplated that a gear assembly or other form of transmission may be disposed between the motor 38 and the drill chuck 36 to transfer torque from the motor 38 to the drill chuck 36 to rotate the drill chuck 36. In one configuration, the motor 38 comprises a DC motor. The surgical drill assembly 32 may comprise a battery (not shown) to supply power to the motor 38. The surgical drill assembly 32 may also comprise a trigger assembly 42 coupled to the housing 40. The trigger assembly 42 includes a trigger 44 movable relative to the housing 40. The trigger assembly 42 may be operatively coupled to the motor 38 such that the motor 38 is configured to rotate the drill chuck 36 in response to actuation of the trigger 44.

The surgical drill assembly 32 may also include a fluid coupler 46 configured to be attached to a shank portion 52 of the surgical drill bit 34 to facilitate the transfer of fluid from a fluid source to enter one or more inner channels 82 of the surgical drill bit 34. The one or more inner channels 82 of the surgical drill bit 34 will be described in greater detail further below. The fluid coupler 46 is configured to prevent leakage of fluid outside the one or more inner channels while fluid is being supplied to the surgical drill bit 34. The fluid coupler 46 is also configured to dynamically seal the surgical drill bit 34 while the surgical drill bit 34 is being rotated by the drill chuck 36.

The housing 40 of the surgical drill assembly 32 shown in FIG. 1 comprises a pistol-grip shaped configuration to be held by a user. It is contemplated that the housing 40 may comprise a configuration having another shape to be held by the user. It is also contemplated that the surgical drill assembly 32 may be configured as an end effector for a robotic arm. One such end effector that employs a drill chuck 36 and a fluid coupler 46 is disclosed in U.S. Patent Publication No. 2017/0119421 entitled "End Effector with Liquid Delivery" and filed on Jan. 12, 2017, which is hereby incorporated by reference in its entirety.

In FIG. 1, the motor 38, the drill chuck 36, and the fluid coupler 46 are shown schematically. The motor 38 may be cannulated such that the surgical drill bit 34, the motor 38, and the fluid coupler 46 are each arranged along the same axis. In other words, the surgical drill bit 34 may pass through a center of the motor 38 to be coupled to the fluid coupler 46. In other configurations, the motor 38 may be offset from the axis AX of the surgical drill bit 34 and the fluid coupler. One such configuration is described and illustrated in U.S. Patent Publication No. 2017/0119421.

Figure 3:
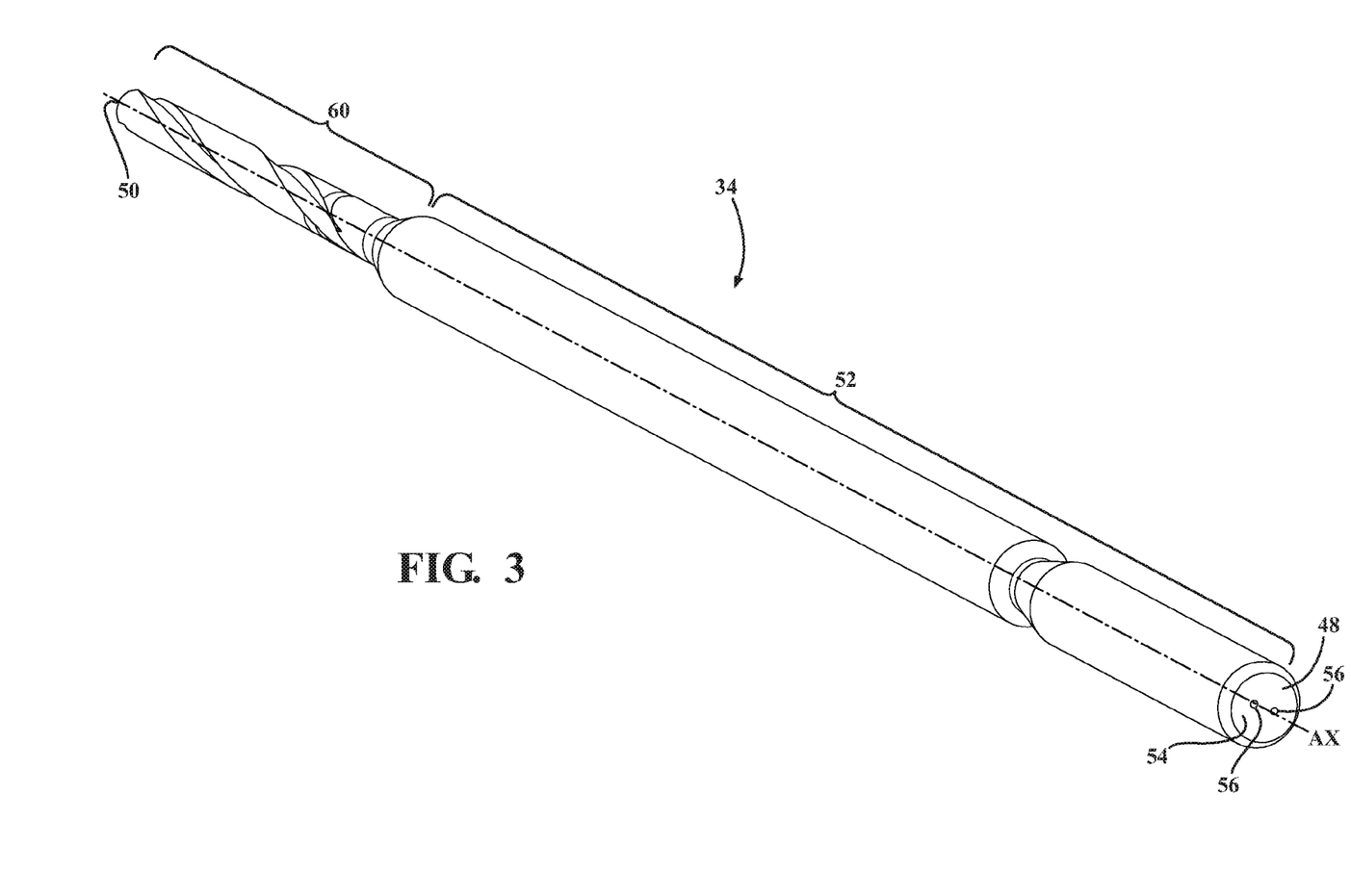
FIG. 3 is a perspective view of the surgical drill bit.

Referring to FIG. 3, the surgical drill bit 34 comprises a generally cylindrical body extending along a drill bit axis AX between proximal 48 and distal 50 ends. The surgical drill bit 34 has a shank portion 52 extending distally along the drill bit axis AX from the proximal end 48. The shank portion 52 is configured to be coupled to and rotated by the drill chuck 36. A proximal surface 54 of the shank portion 52 defines a proximal opening 56. In the configuration illustrated in FIG. 3, the proximal surface 54 of the shank portion 52 defines two proximal openings 56. It is contemplated that the proximal surface 54 of the shank portion 52 may define three or more proximal openings 56. It is also contemplated that the proximal surface 54 of the shank portion 52 may define a single proximal opening 56. In the configuration illustrated in FIG. 3, the proximal opening 56 is defined offset from the drill bit axis AX such that the drill bit axis AX does not pass through the proximal opening 56. It is contemplated that in other configurations the proximal opening 56 may be defined along the drill bit axis AX such that the drill bit axis AX passes through the proximal opening 56.

The shank portion 52 of the surgical drill bit 34 may comprise a recess 58 for facilitating coupling between the shank portion 52 of the surgical drill bit 34 and the drill chuck 36. It is contemplated that the shank portion 52 may additionally or alternatively comprise other coupling features such as a tang, a reduced diameter, a hex-head, or another like coupling feature to facilitate coupling between the shank portion 52 of the surgical drill bit 34 and the drill chuck 36.

Figures 4, 5:
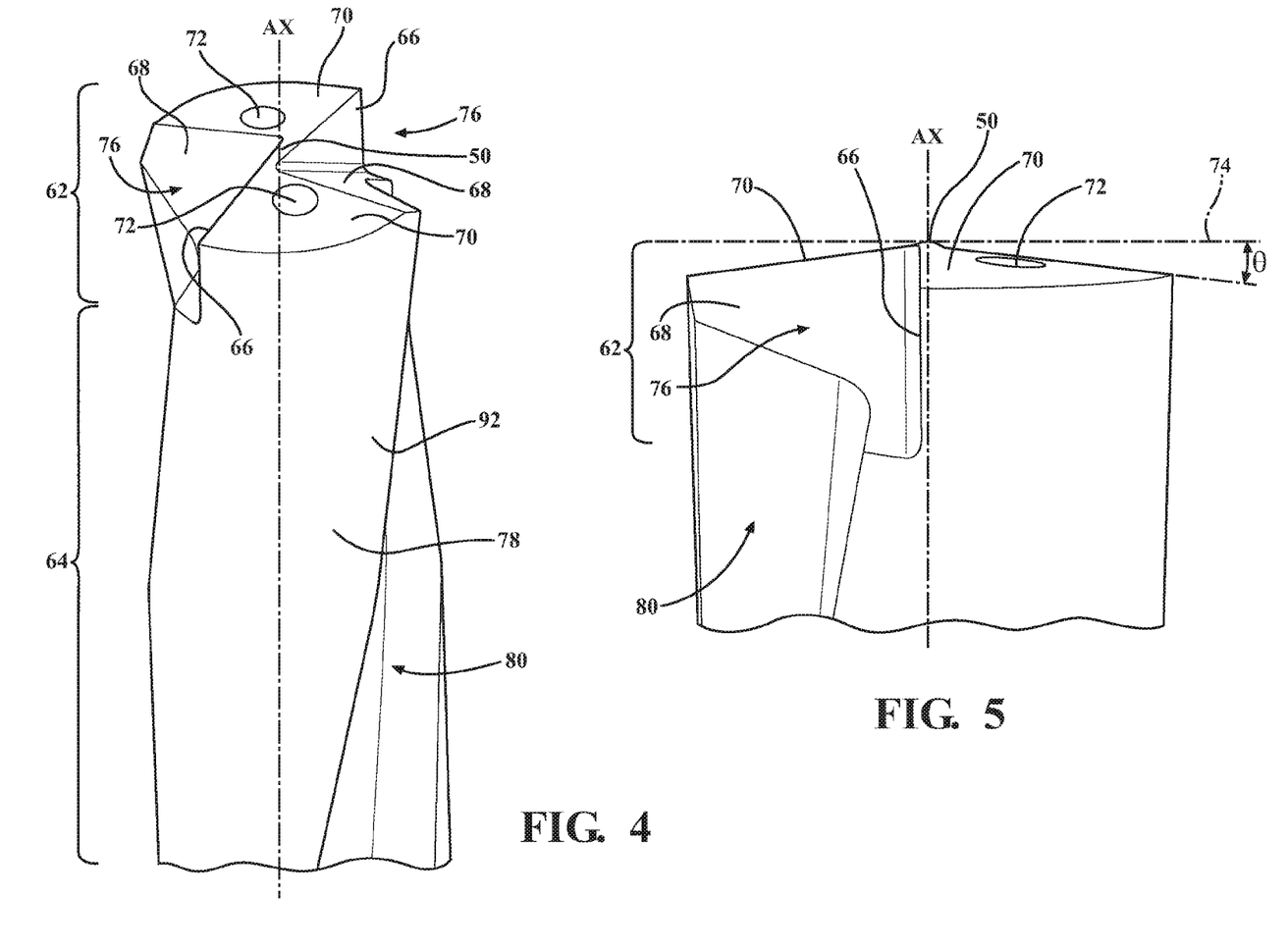
FIG. 4 is a perspective view of a drilling portion of the surgical drill bit.
FIG. 5 is an elevation view of a distal cutting region of the drilling portion of the surgical drill bit.

Referring to FIGS. 4 and 5 the surgical drill bit 34 includes a drilling portion 60. The drilling portion is configured to drill through bone. The drilling portion 60 extends distally along the drill bit axis AX from the shank portion 52 to the distal end 50 of the surgical drill bit 34. The drilling portion 60 comprises a distal cutting region 62 adjacent the distal end 50 of the surgical drill bit 34 and a fluted region 64 disposed between the shank portion 52 of the surgical drill bit 34 and the distal cutting region 62 of the drilling portion 60 of the surgical drill bit 34.

The distal cutting region 62 comprises a rake surface 66 for cutting into bone while drilling. The rake surface 66 illustrated in FIGS. 4 and 5 is generally planar and generally parallel to the drill bit axis AX. In other configurations, the rake surface 66 may not be parallel to the drill bit axis AX. In still other configurations, the rake surface 66 many not be planar. The distal cutting region 62 may also comprise a clearance surface 68 for directing bone chips away from the bone during drilling.

The distal cutting region 62 further comprises a flank surface 70 disposed between the rake surface 66 and the clearance surface 68. The flank surface 70 may define a distal opening 72. In the configuration illustrated in FIGS. 4 and 5, the flank surface 70 defines two distal openings 72. It is contemplated that the flank surface 70 may define three or more distal openings 72. It is also contemplated that the flank surface 70 may define a single distal opening 72. In the configuration illustrated in FIGS. 4 and 5, the distal opening 72 is defined offset from the drill bit axis AX such that the drill bit axis AX does not pass through the distal opening 72. It is contemplated that in other configurations the distal opening 72 may be defined along the drill bit axis AX such that the drill bit axis AX passes through the distal opening 72. The flank surface 70 may be configured to abut the bone during drilling such that the distal opening 72 is occluded by the bone while the rake surface 66 is cutting into the bone.

As shown in FIG. 5, the flank surface 70 may be generally planar and generally perpendicular to the drill bit axis AX. In one configuration, the flank surface 70 may be disposed at an angle θ between zero degrees and fifteen degrees from a reference plane 74 that is perpendicular to the drill bit axis AX. In another configuration, the angle θ between the flank surface 70 and the reference plane 74 may be between zero degrees and ten degrees.

In other configurations, the flank surface 70 may be conical or frustoconical. In one such configuration, the angle θ between the flank surface 70 and the reference plane 74 may be between zero degrees and fifteen degrees. In another such configuration, the angle θ between the flank surface 70 and the reference plane 74 between zero degrees and ten degrees. It is contemplated that as the angle between the conical or frustoconical flank surface 70 and the reference plane 74 approaches zero degrees (i.e., the flank surface 70 is parallel to the reference plane 74), the conical or frustoconical flank surface 70 approximates a planar surface.

In the configuration illustrated in FIGS. 4 and 5, the distal cutting region 62 of the drilling portion 60 of the surgical drill bit 34 comprises two rake surfaces 66, two flank surfaces 70, and two clearance surfaces 68 arranged circumferentially about the drill bit axis AX. In such a configuration, the flank surfaces 70 and the clearance surfaces 68 are arranged consecutively such that each rake surface 66 and one of the clearance surfaces 68 collectively define a relief 76 where bone fragments or other tissue may accumulate as the rake surface 66 is cutting through bone. In other configurations, the distal cutting region 62 of the drilling portion 60 of the surgical drill bit 34 comprises three or more of each of the rake, flank, and clearance surfaces 66, 70, 68. In still other configurations, the distal cutting region 62 of the drilling portion 60 of the surgical drill bit 34 comprises one of each of the rake, flank, and clearance surfaces 66, 70, 68.

As shown in FIGS. 3 and 4, the fluted region 64 of the surgical drill bit 34 may extend proximally toward the shank portion 52 from the distal cutting region 62. The fluted region 64 may comprise two lands 78 extending between the shank portion 52 and the distal cutting region 62. The lands 78 may be helically disposed along the fluted region 64 of the drilling portion 60 of the surgical drill bit 34. The lands 78 define two flutes 80 that likewise helically extend between the shank portion 52 and the distal cutting region 62. In another configuration, the fluted region 64 may comprise three or more lands 78 extending between the shank portion 52 and the distal cutting region 62 to define three or more flutes 80. In a further configuration, the fluted region 64 may comprise one land 78 extending between the shank portion 52 and the distal cutting region 62 to define a single flute 80. In such a configuration, the land 78 may not be distinguishable from the shank portion 52 of the surgical drill bit 34 but for the flute 80. It is contemplated that the lands 78 and the flutes 80 defined by the lands 78 may not be disposed helically. The lands 78 and the flutes 80 may instead extend linearly along the fluted region 64 of the drilling portion 60 of the surgical drill bit 34. It is also contemplated that in some configurations, the drilling portion 60 of the surgical drill bit 34 does not include a fluted region 64. The lands 78 may comprise cutting edges to cut through bone in a lateral direction.

Each of the flutes 80 may be in communication with one of the reliefs 76 defined by the clearance surface 68 and the rake surface 66 of the distal cutting region 62 of the drilling portion 60 of the surgical drill bit 34. In this manner, the bone fragments or other tissue may accumulate in the relief 76 and the clearance surface 68 may direct the bone fragments or other tissue into the flutes 80 of the fluted region 64 to direct the bone fragments or other tissue from the distal cutting region 62 while cutting through bone. In many configurations, the number of flutes 80 are equal to the number of reliefs 76.

Figures 6, 7:
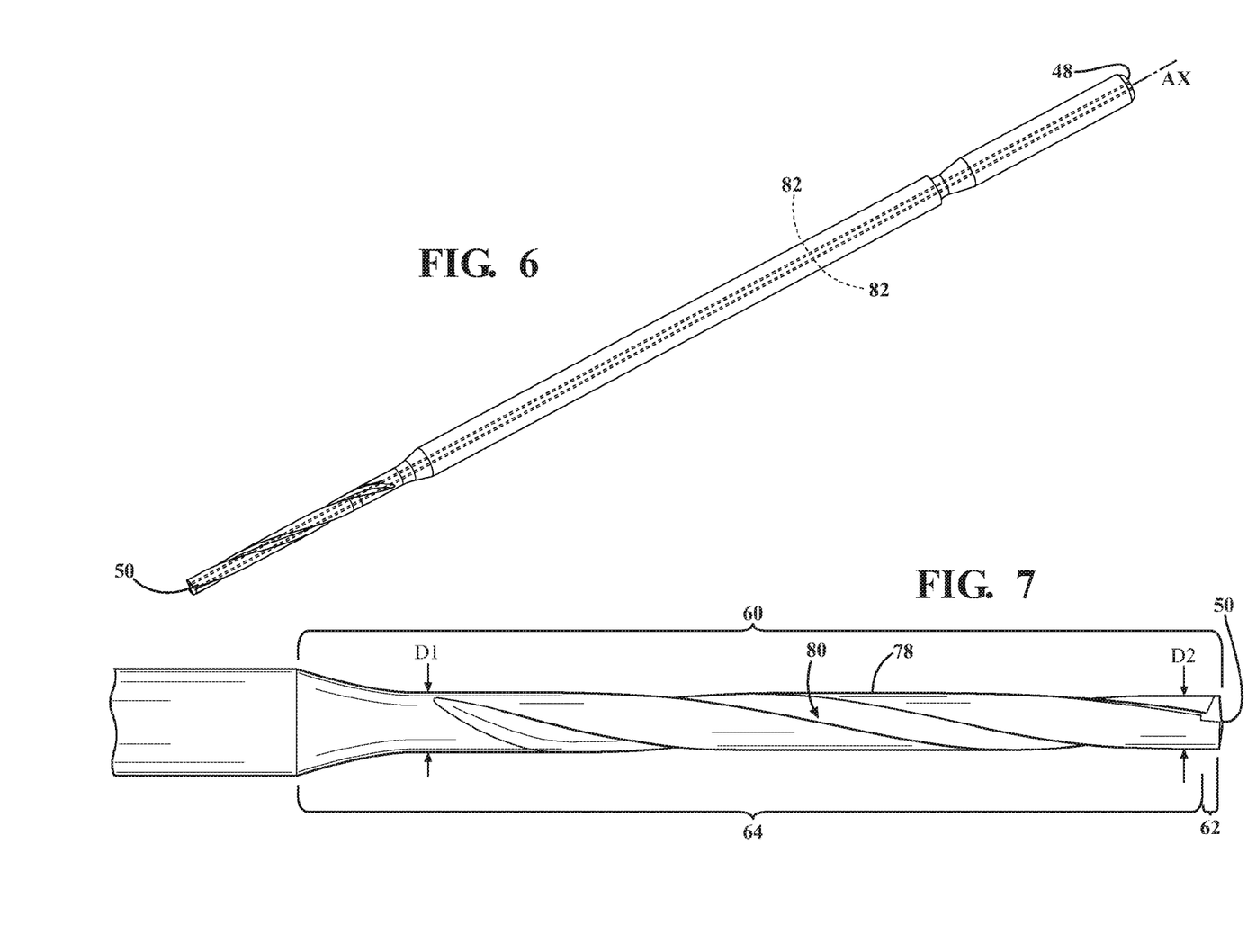
FIG. 6 is another perspective view of one configuration of the surgical drill bit with two inner channels extending from a proximal end of the surgical drill bit to a distal end of the surgical drill bit.
FIG. 7 is an elevation view of the drilling portion of the surgical drill bit illustrating a taper from the proximal end of the drilling portion to a distal end of the drilling portion.

As shown in FIG. 6, the shank and drilling portions 52, 60 of the surgical drill bit 34 collectively define an inner channel 82 in fluid communication with the proximal and distal openings 56, 72. The fluid may be transferred from a fluid source through the fluid coupler 46 of the surgical drill assembly 32 and introduced through the proximal opening 56 of the shank portion 52 of the surgical drill bit 34. The fluid may then travel through the inner channel 82 and out the distal opening 72. The distal opening 72 functions as an outlet to permit fluid to exit the surgical drill bit 34 when the distal opening 72 is not occluded. When the distal opening 72 is occluded by bone or tissue, fluid pressure may be established within the inner channel 82 and along the fluid line from the fluid source. In the configuration shown in FIG. 6, two inner channels 82 are shown—one for each set of proximal and distal openings 56, 72. It is contemplated that three or more inner channels 82 may be defined in the surgical drill bit 34 for three or more proximal and distal openings 56, 72. It is also contemplated that a single inner channel 82 may be defined in the surgical drill bit 34 for one proximal and distal opening 56, 72. It is further contemplated that the number of inner channels 82 and the number of distal and proximal openings 56, 72 may not be equal. For example, the surgical drill bit 34 may define a single proximal opening 56 and two distal openings 72. An inner channel 82 may extend along the surgical drill bit 34 and eventually split into two paths to be in fluid communication with each distal opening 72.

As shown in FIG. 7, the drilling portion 60 of the surgical drill bit 34 may taper toward the drill bit axis AX from the shank portion 52 of the surgical drill bit 34 to the distal end 50 of the surgical drill bit 34. In other words, the diameter D2 of the surgical drill bit 34 at the distal end 50 of the surgical drill bit 34 is smaller than the diameter of the surgical drill bit 34 at a proximal end of the drilling portion 60 of the surgical drill bit 34. In such a configuration, the lands 78 of the fluted region 64 comprise the cutting edges to cut through bone while the surgical drill bit 34 is plunged into bone.

Figure 2:
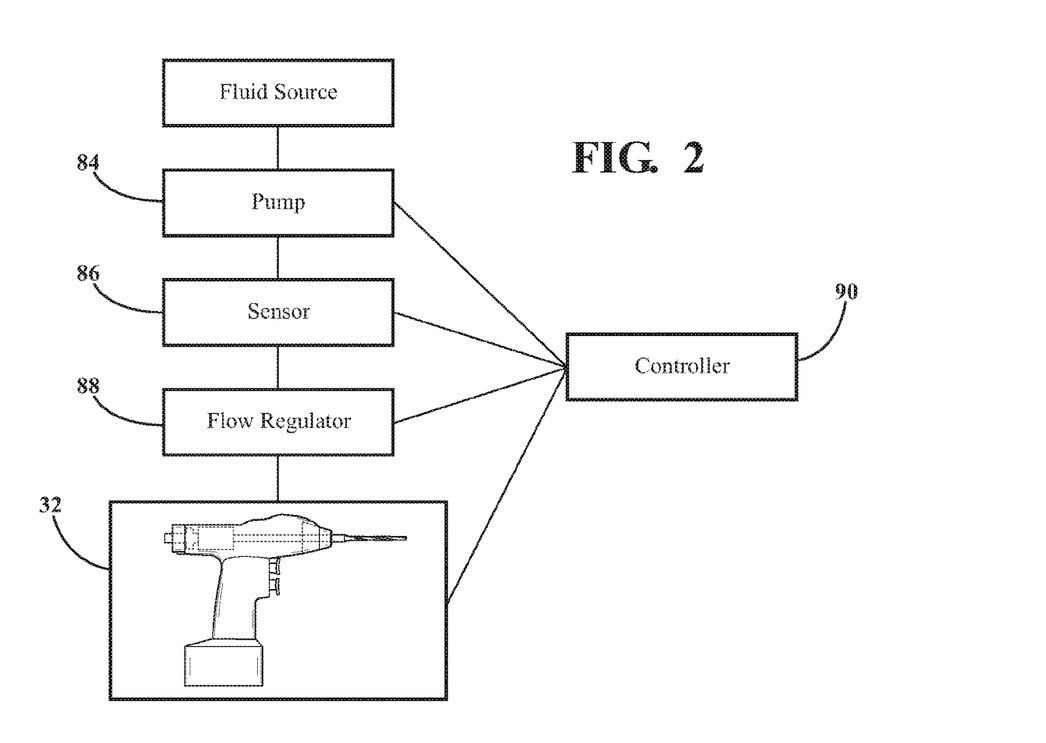
FIG. 2 is a schematic view of the surgical drilling system.

As schematically shown in FIG. 2, the surgical drilling system 30 may comprise a pump 84 configured to transfer fluid from the fluid source to the fluid coupler of the surgical drill assembly 32 and into the inner channel 82 of the surgical drill bit 34 through the proximal opening 56 of the surgical drill bit 34.

As schematically shown in FIG. 2, the surgical drilling system 30 may comprise a sensor 86 disposed in fluid communication with the inner channel 82 of the surgical drill bit 34 and configured to generate a signal responsive to a characteristic of the fluid being transferred to the inner channel 82 of the surgical drill bit 34. The characteristic of the fluid being transferred to the inner channel 82 of the surgical drill bit 34 may comprises one or more characteristics selected from a fluid velocity, a fluid volumetric flow rate, and a fluid pressure. It is contemplated that the sensor 86 may generate the signal responsive to another characteristics of the fluid being transferred to the inner channel 82 of the surgical drill bit 34.

As schematically shown in FIG. 2, the surgical drilling system 30 may comprise a flow regulator 88 such as a control valve disposed in fluid communication with the inner channel 82 of the surgical drill bit 34 to control the flow of fluid from the pump 84 to the inner channel 82 of the surgical drill bit 34. In other configurations, the pump 84 may be operated to regulate the flow of fluid to the inner channel 82 of the surgical drill bit 34. It is contemplated that devices other than a control valve may be employed to regulate the flow of fluid being introduced into the inner channel 82 of the surgical drill bit 34.

The surgical drilling system 30 may comprise a controller 90 configured to receive the signal from the sensor 86 and determine a characteristic of the drilling medium at the distal opening 72 of the surgical drill bit 34 based on the signal. The controller 90 may also be configured to generate signals to the pump 84 and the flow regulator 88 to operate the pump 84 and flow regulator 88 in response to signals received from the sensor 86. The characteristic of the drilling medium at the distal opening 72 of the surgical drill bit 34 may be a presence of tissue or a type of tissue (e.g., cortical bone or cancellous bone). Each type of tissue may have a certain physical characteristic that distinguishes it from another type of tissue. One such physical characteristic is porosity. One type of tissue occluding the distal opening 72 of the surgical drill bit 34 may cause a change in fluid pressure or fluid flow due to its porosity that is different from another type of tissue occluding the distal opening 72 of the surgical drill bit 34.

In one configuration, the controller 90 may receive a signal from the sensor 86 and determine from the signal that the surgical drill bit 34 has broken through a last layer of bone such that the distal cutting region 62 of the drilling portion 60 is no longer cutting bone. The sensor 86 may generate such a signal if there is certain drop in pressure or a certain increase in fluid flow resulting from the distal opening 72 no longer being occluded. In another configuration, the controller 90 may receive a signal from the sensor 86 and determine from the signal a position of the surgical drill bit 34 in the bone. More specifically, the controller 90 may be configured to receive the signal from the sensor 86 and determine that the surgical drill bit 34 has transitioned from a first bone structure to a second bone structure (e.g. cortical bone to cancellous bone). The sensor 86 may be configured to generate one signal responsive to the certain drop in pressure or increase in fluid flow indicating bone breakthrough and another signal responsive to the certain drop in pressure or increase in fluid flow indicating a transition of bone structure.

In order to obtain accurate signals of changes in characteristics of the fluid being transferred to the inner channel 82 of the surgical drill bit 34, it is advantageous to mitigate the leakage of fluid while the surgical drill bit 34 is cutting through bone and the distal opening 72 is occluded. Certain features of the surgical drill bit 34 may be employed to mitigate fluid leakage while the surgical drill bit 34 is cutting through bone. For example, the flank surface 70 of the distal cutting region 62 of the surgical drill bit 34 defining the distal opening 72 ensures the distal opening 72 will be occluded while cutting through bone. It is advantageous for the distal opening 72 to be defined by the flank surface 70 rather than the rake surface 66 or the clearance surface 68. If the distal opening 72 were defined by the rake surface 66, bone fragments or tissue may be forced into the inner channel 82 through the distal opening 72. If the distal opening 72 were defined by the clearance surface 68, the distal opening 72 would not be occluded by bone during cutting and fluid may leak out and be directed into the flutes 80. The flank surface 70 being generally planar is another feature that mitigates fluid leakage while the surgical drill bit 34 is cutting through bone. While the surgical drill bit 34 is drilling through bone, the generally planar surface ensures any gaps between the flank surface 70 and the bone are mitigated. The taper of the drilling portion 60 of the surgical drill bit 34 is another feature that mitigates fluid leakage while the surgical drill bit 34 is cutting through bone. The tapered surgical drill bit 34 ensures that the drilling portion 60, including the fluted region 64, is always contacting the bone while drilling.

After the controller 90 determines there is a breakthrough or a transition of bone structure, the controller 90 may generate one or more signals to the surgical drill assembly 32 to arrest the drill chuck 36 to stop the surgical drill bit 34 from rotating. In configurations where the surgical drilling system 30 includes a robotic arm and an end effector, the controller 90 may be configured to operate the robotic arm to cease movement of the robot arm in addition to arresting the drill chuck 36. For instance, the robotic arm may have been configured to axially move or "feed" the surgical drill bit 34 along the drill bit axis AX while the surgical drill bit 34 was cutting through bone. When the controller 90 may be configured to stop the robotic arm from continuing to move the surgical drill bit 34 into the bone.

Figure 8:
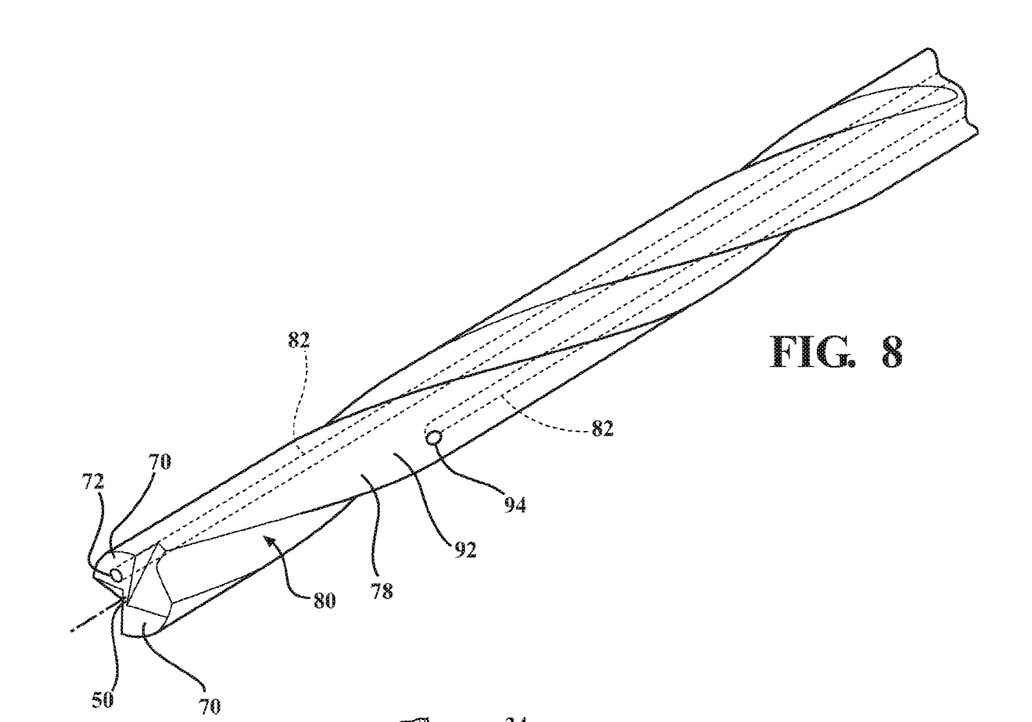
FIG. 8 is a perspective view of another configuration of the surgical drill bit with an inner channel extending along a drill bit axis of the surgical drill bit from the proximal end of the surgical drill bit to a land of a fluted region of the drilling portion of the surgical drill bit.

In one configuration shown in FIG. 8, the controller 90 may be able to determine a breakthrough in a lateral direction relative to the surgical drill bit 34 or a change in bone structure in a lateral direction relative to the surgical drill bit 34. In such a configuration, an outer lateral surface 92 of one of the lands 78 of the fluted region 64 may define a lateral opening 94. Fluid may be transferred from the fluid source through the fluid coupler 46 of the surgical drill assembly 32 and introduced through the proximal opening 56 of the shank portion 52 of the surgical drill bit 34. The fluid may then travel through the inner channel 82 and out the lateral opening 94. The lateral opening 94 functions as another outlet to permit fluid to exit the surgical drill bit 34 when the lateral opening 94 is not occluded.

The outer lateral surface of the lands 78 faces away from the flutes 80 of the fluted region 64. One of the inner channels 82 may be in fluid communication with one of the proximal openings 56 and the lateral opening 94. As the outer lateral surface 92 of the lands 78 faces away from the flute 80, the lateral opening 94 may be occluded by bone while the surgical drill bit 34 is cutting through bone to establish fluid pressure within the inner channel 82. In one configuration, the distal cutting region 62 of the surgical drill bit 34 is free of any distal openings 72 in fluid communication with any of the inner channels 82 such that the controller 90 determines a breakthrough or change in bone structure in the lateral direction only.

In some configurations, the surgical drill bit 34 includes both distal and lateral openings 72, 94 with separate inner channels 82 and proximal openings 56 for each of the distal and lateral openings 72, 94. In such a configuration, the inner channel 82 in fluid communication with the distal opening 72 may have a first geometrical configuration and the inner channel 82 in fluid communication with the lateral opening 94 may have a second geometrical configuration different from the first geometrical configuration. The geometrical configurations may be the cross-sectional area of the inner channels. Each of the inner channels 82 may have a different cross-sectional area. The difference in geometrical configurations may result in distinct pressure drops/rises or flow rate gains/losses. The sensor 86 may be configured to generate a first signal responsive to occlusion of the distal opening 72 and a second signal different from the first signal responsive to occlusion of the lateral opening 94. The controller 90 may be configured to receive the first and second signals from the sensor 86 and determine a breakthrough or change in bone structure responsive to the first and second signals.

Figure 9:
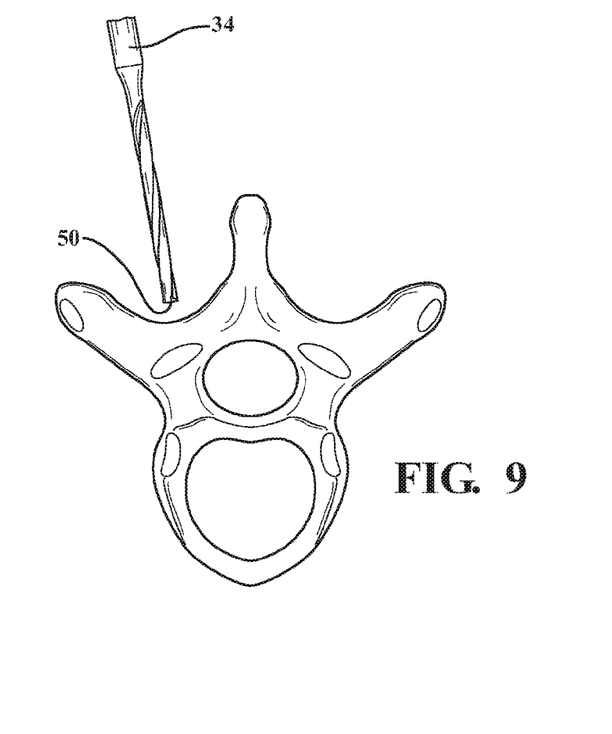
FIG. 9 is a plan view of an exemplary configuration of the surgical drill bit before entering bone or other tissue.
Figure 10:
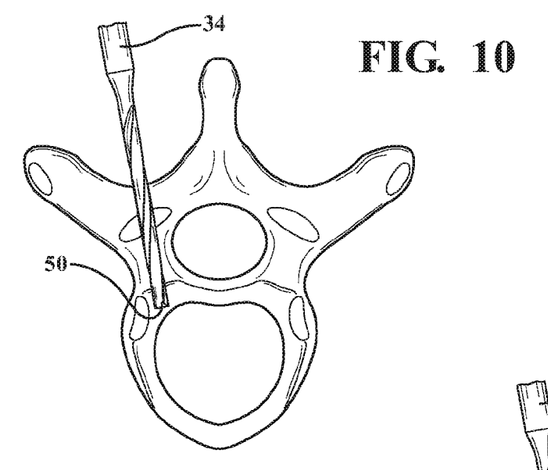
FIG. 10 is a plan view of an exemplary configuration of the surgical drill bit with the surgical drill bit having bored through some bone and tissue.
Figure 11:
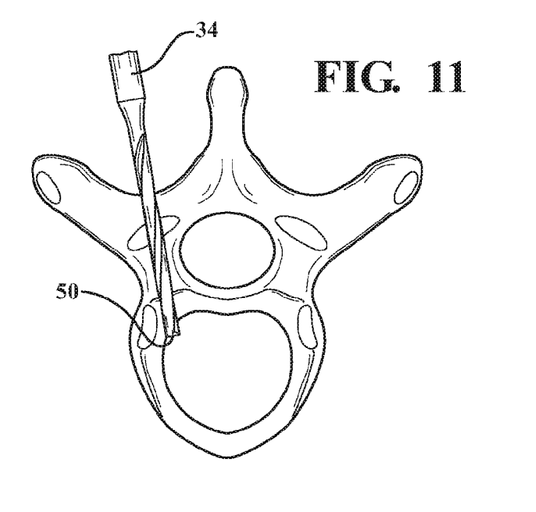
FIG. 11 is a plan view of an exemplary configuration of the surgical drill bit with the distal cutting region of the surgical drill bit having bored through the bone and tissue.

In FIGS. 9-11, an exemplary configuration of the surgical drill bit 34 drilling through bone and the distal end 50 of the surgical drill bit 34 transitioning from one tissue type to another for a spinal drilling application. In FIG. 9, the surgical drill bit 34 is prepared to enter vertebral bone. The surgical drill bit 34 may be rotated by the drill chuck 36 and motor 38 and the surgical drill bit 34 may be plunged into the vertebral bone to begin cutting the vertebral bone. Shortly before or shortly after the surgical drill bit 34 begins cutting into bone, the pump 84 may draw fluid from the fluid source and force fluid into the inner channel 82 of the surgical drill bit 34.

As the surgical drill bit 34 is cutting through bone, the distal opening 72 is occluded and leakage of the fluid out the distal opening 72 is mitigated. Fluid pressure may be established in the inner channel 82 while the distal opening 72 is occluded. While the surgical drill bit 34 is advanced through the bone and continues cutting the bone to the position shown in FIG. 10, the fluid pressure and/or flow rate may fluctuate within an operational range. The deviation of the fluid pressure and/or flow rate within the operational range may not be enough to cause the controller 90 to stop the surgical drill bit 34 from rotating.

After the surgical drill bit 34 has broken through an outer layer of a first tissue type, as shown in FIG. 11, the sensor 86 may generate a signal to the controller 90 responsive to the fluid pressure and/or flow rate fluctuating outside of the operational range and the controller 90 may determine the surgical drill bit 34 has transitioned to cutting a different type of tissue. The controller 90 may be configured to arrest the drill chuck 36 to stop the surgical drill bit 34 from continuing to cut through bone and/or other tissue.

Figure 12:
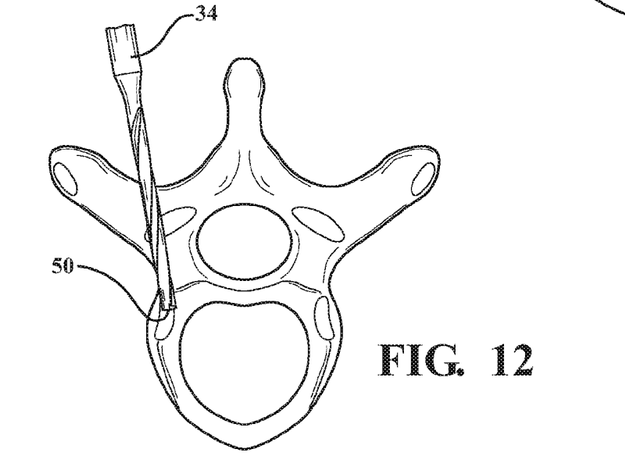
FIG. 12 is a plan view of an exemplary configuration of the surgical drill bit with the fluted region of the surgical drill bit.

In FIG. 12, another exemplary configuration of the surgical drill bit 34 for a spinal drilling application is shown. In this configuration, instead of the distal end 50 of the surgical drill bit 34 transitioning from one type of tissue to another, a lateral or partial breach is shown. In this configuration, the surgical drill bit 34 may have begun drilling in the same manner as described above and with reference to FIGS. 9 and 10. However, the trajectory of the surgical drill bit 34 may have been plunged at an incorrect angle or location such that the fluted region 64 may break through the outer layer of the bone before the distal end 50 of the surgical drill bit 34 completely breaks through the outer layer of the bone or transitions from one type of tissue to another. In such an instance when the fluted region 64 of the surgical drill bit 34 breaks through, the lateral opening 94 of the surgical drill bit 34 may cease being occluded and the sensor 86 may generate a signal to the controller 90 responsive to the fluid pressure and/or flow rate fluctuating outside of the operational range and the controller 90 may be configured to arrest the drill chuck 36 to stop the surgical drill bit 34 from continuing to cut through bone and/or other tissue.

The foregoing description is merely illustrative in nature and is in no way intended to limit the disclosure, its application, or uses. The broad teachings of the disclosure can be implemented in a variety of forms. Therefore, while this disclosure includes particular configurations, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the configurations is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In this application, including the definitions below, the term "controller 90" may be replaced with the term "circuit." The term "controller 90" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller 90 may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller 90 may communicate with other controllers using the interface circuit(s). Although the controller 90 may be depicted in the present disclosure as logically communicating directly with other controllers, in various implementations the controller 90 may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller 90 may be distributed among multiple controllers that are connected via the communications system. For example, multiple controllers may implement the same functionality distributed by a load balancing system. In a further example, the functionality of the controller 90 may be split between a server (also known as remote, or cloud) controller and a client (or, user) controller.

Some or all hardware features of the controller 90 may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SSENSORLINK, and Python®.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

The invention is intended to be defined in the independent claims, with specific features laid out in the dependent claims, wherein the subject matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

CLAUSES

I. A surgical drill bit configured for bone drilling and configured to be coupled to a surgical drill assembly that is configured to determine a characteristic of a drilling medium from a characteristic of fluid flow, said surgical drill bit comprising:
a shank portion extending distally along a drill bit axis from a proximal end, the shank portion configured to be coupled to and rotated by a drill chuck of the surgical drill assembly, and the shank portion having a proximal surface defining a proximal opening; and
a drilling portion for drilling through bone, the drilling portion extending distally along the drill bit axis from the shank portion to a distal end, the drilling portion having a distal cutting region comprising:
a rake surface for cutting into a bone while drilling,
a clearance surface for directing bone chips away from the bone during drilling, and
a flank surface disposed between the rake surface and the clearance surface, the flank surface defining a distal opening, and the flank surface configured to abut the bone such that the distal opening is occluded by the bone while the rake surface is cutting into the bone;
wherein the shank and drilling portions collectively define an inner channel in fluid communication with the proximal and distal openings, and wherein the distal opening is configured to be occluded by the bone during drilling to establish fluid pressure within the inner channel.

II. The surgical drill bit of clause I, wherein the flank surface is generally planar.

III. The surgical drill bit of clause II, wherein the flank surface is generally perpendicular to the drill bit axis.

IV. The surgical drill bit of any one of clauses I to III, wherein the drilling portion further comprises a fluted region extending proximally toward the shank portion from the distal cutting region.

V. The surgical drill bit of any one of clauses I to IV, wherein the drilling portion tapers toward the drill bit axis from the shank portion to the distal end.

VI. The surgical drill bit of any one of clauses I to V, wherein the distal opening is offset from the drill bit axis.

VII. A surgical drilling system configured for bone drilling and configured to determine a characteristic of a drilling medium from a characteristic of fluid flow, said surgical drilling system comprising:
a drill chuck configured to be rotated by a motor;
a surgical drill bit configured to be coupled to the drill chuck, the surgical drill bit comprising:
a shank portion extending distally along a drill bit axis from a proximal end, the shank portion configured to be coupled to and rotated by the drill chuck, and the shank portion having a proximal surface defining a proximal opening, and
a drilling portion for drilling through bone, the drilling portion extending distally along the drill bit axis from the shank portion to a distal end, the drilling portion having a distal cutting region comprising:
a rake surface for cutting into a bone while drilling,
a clearance surface for directing bone chips away from the bone during drilling, and
a flank surface disposed between the rake surface and the clearance surface, the flank surface defining a distal opening, and the flank surface configured to abut the bone such that the distal opening is occluded by the bone while the rake surface is cutting into the bone,
wherein the shank and drilling portions collectively define an inner channel in fluid communication with the proximal and distal openings, and wherein the distal opening is configured to be occluded by the bone during drilling to establish fluid pressure within the inner channel;

a pump configured to transfer fluid from a fluid source into the inner channel of the surgical drill bit through the proximal opening of the surgical drill bit;

a sensor disposed in fluid communication with the inner channel and configured to generate a signal responsive to a characteristic of the fluid being transferred to the inner channel of the surgical drill bit; and a controller configured to receive the signal from the sensor and determine a characteristic of the drilling medium at the distal opening of the surgical drill bit based on the signal.

VIII. The surgical drilling system of clause VII, wherein the flank surface of the surgical drill bit is generally planar.

IX. The surgical drilling system of clause VIII, wherein the flank surface of the surgical drill bit is generally perpendicular to the drill bit axis.

X. The surgical drilling system of any one of clauses VII to IX, wherein the drilling portion of the surgical drill bit further comprises a fluted region extending proximally toward the shank portion from the distal cutting region.

XI. The surgical drilling system of any one of clauses VII to X, wherein the drilling portion of the surgical drill bit tapers toward the drill bit axis from the shank portion of the surgical drill bit to the distal end of the surgical drill bit.

XII. The surgical drilling system of any one of clauses VII to XI, wherein the distal opening of the surgical drill bit is offset from the drill bit axis.

XIII. The surgical drilling system of any one of clauses VII to XII, wherein the characteristic of the fluid being transferred to the inner channel of the surgical drill bit comprises one or more characteristics selected from a fluid velocity, a fluid volumetric flow rate, and a fluid pressure.

XIV. The surgical drilling system of any one of clauses VII to XIII, wherein the characteristic of the drilling medium at the distal opening of the surgical drill bit comprises one characteristic selected from a tissue presence and a tissue type.

XV. The surgical drilling system of any one of clauses VII to XIV, wherein the controller is configured to receive the signal from the sensor and determine a breakthrough event has occurred based on the signal from the sensor.

XVI. The surgical drilling system of clause XV, wherein the breakthrough event comprises one event selected from the surgical drill bit breaching through the bone and the surgical drill bit transitioning from a first bone structure to a second bone structure.

XVII. The surgical drilling system of any one of clauses XV to XVI, wherein the controller is configured to arrest the drill chuck to stop the surgical drill bit from rotating responsive to the controller determining a breakthrough event has occurred.

XVIII. The surgical drilling system of any one of clauses XV to XVII, further comprising a robot arm coupled to the drill chuck and configured to axially move the drill chuck and the surgical drill bit along the drill bit axis, wherein the controller is configured to arrest the robot arm from axially moving responsive to the controller determining a breakthrough event has occurred.

XIX. The surgical drilling system of any one of clauses VII to XVIII, wherein the controller is configured to determine a position of the surgical drill bit in the bone based on the signal from the sensor.

XX. A surgical drilling system configured for bone drilling and configured to determine a characteristic of a drilling medium from a characteristic of fluid flow, said surgical drilling system comprising:

a drill chuck configured to be rotated by a motor;

a surgical drill bit extending from a proximal end to a distal end along a drill bit axis, and the surgical drill bit configured to be coupled to the drill chuck and configured to rotate with the drill chuck, and the surgical drill bit comprising:

a shank portion adjacent the proximal end of the surgical drill bit, the shank portion configured to be coupled to and rotated by the drill chuck, and the shank portion having a proximal surface defining a proximal opening, and a drilling portion for drilling through bone, the drilling portion extending distally along the drill bit axis from the shank portion to the distal end of the surgical drill bit, the drilling portion comprising:

a distal cutting region adjacent the distal end of the surgical drill bit for plunging into the bone, and a fluted region disposed between the shank portion and the distal cutting region, the fluted region comprising a lateral surface defining a lateral opening, wherein the shank and drilling portions collectively define an inner channel in fluid communication with the proximal and lateral openings, and wherein the lateral opening is configured to be occluded by the bone during drilling to establish fluid pressure within the inner channel;

a pump configured to transfer fluid from a fluid source into the inner channel of the surgical drill bit through the proximal opening of the surgical drill bit;

a sensor disposed in fluid communication with the inner channel and configured to generate a signal responsive to a characteristic of the fluid being transferred to the inner channel of the surgical drill bit; and a controller configured to receive the signal from the sensor and determine a characteristic of the drilling medium at the lateral opening of the surgical drill bit based on the signal.

XXI. The surgical drilling system of clause XX, wherein the drilling portion of the surgical drill bit tapers toward the drill bit axis from the shank portion of the surgical drill bit to the distal end of the surgical drill bit.

XXII. The surgical drilling system of any one of clauses XX to XXI, wherein the characteristic of the fluid being transferred to the inner channel of the surgical drill bit comprises one or more characteristics selected from a fluid velocity, a fluid volumetric flow rate, and a fluid pressure.

XXIII The surgical drilling system of any one of clauses XX to XXII, wherein the characteristic of the drilling medium at the lateral opening of the surgical drill bit comprises one characteristic selected from a tissue presence and a tissue type.

XXIV. The surgical drilling system of any one of clauses XX to XXIII, wherein the controller is configured to receive the signal from the sensor and determine a breakthrough event has occurred based on the signal from the sensor.

XXV. The surgical drilling system of clause XXIV, wherein the breakthrough event comprises one event selected from the surgical drill bit breaching through the bone and the surgical drill bit transitioning from a first bone structure to a second bone structure.

XXVI. The surgical drilling system of any one of clauses XXIV to XXV, wherein the controller is configured to arrest the drill chuck to stop the surgical drill bit from rotating responsive to the controller determining a breakthrough event has occurred.

XXVII. The surgical drilling system of any one of clauses XXIV to XXVI, further comprising a robot arm coupled to the drill chuck configured to axially move the drill chuck and the surgical drill bit along the drill bit axis, wherein the controller is configured to arrest the robot arm from axially moving responsive to the controller determining a breakthrough event has occurred.

XXVIII. The surgical drilling system of any one of clauses XX to XXVI, wherein the controller is configured to determine a position of the surgical drill bit in the bone based on the signal from the sensor.

XXIX. The surgical drilling system of any one of clauses XX to XXVIII, wherein the fluted region comprises two lands extending between the shank portion and the distal cutting region, and wherein the two lands define a flute between the two lands.

XXX. The surgical drilling system of clause XXIX, wherein one of the two lands comprises the lateral surface that defines the lateral opening, and wherein the lateral surface faces away from the flute.

XXXI. The surgical drilling system of any one of clauses XX to XXX, wherein the distal cutting region of the surgical drill bit is free of an opening in fluid communication with the inner channel.

XXXII. A surgical drilling system configured for bone drilling and configured to determine a characteristic of a drilling medium from a characteristic of fluid flow, said surgical drilling system comprising:
a drill chuck configured to be rotated by a motor;
a surgical drill bit for drilling through bone, the surgical drill bit configured to be coupled to the drill chuck and configured to rotate with the drill chuck, and the surgical drill bit extending distally along a drill bit axis from a proximal end to a distal end, and the surgical drill bit defining:
  a first inner channel extending distally from the proximal end, the first inner channel having a first geometrical configuration, and the first inner channel having a first outlet configured to be occluded during drilling to establish fluid pressure within the first inner channel, and
  a second inner channel extending distally from the proximal end, the second inner channel having a second geometrical configuration different from the first geometrical configuration, and the second inner channel having a second outlet configured to be occluded during drilling to establish fluid pressure within the second inner channel;
a pump configured to transfer fluid from a fluid source into the first and second inner channels of the surgical drill bit;
a sensor disposed in fluid communication with the first and second inner channels and configured to generate a first signal responsive to a first characteristic of the fluid being transferred to the first inner channel of the surgical drill bit corresponding to occlusion of the first outlet, and the sensor configured to generate a second signal different from the first signal responsive to a second characteristic of the fluid being transferred to the second inner channel of the surgical drill bit corresponding to occlusion of the second outlet; and
a controller configured to receive the first and second signals from the sensor and determine a characteristic of the drilling medium at the first and second outlets based on the first and second signals.

XXXIII The surgical drilling system of clause XXXII, wherein the first geometrical configuration comprises a first cross-sectional area and the second geometrical configuration comprises a second cross-sectional area different from the first cross-sectional area.

XXXIV. The surgical drilling system of any one of clauses XXXII to XXXIII, wherein the surgical drill bit comprises a shank portion adjacent the proximal end of the surgical drill bit, the shank portion configured to be coupled to the drill chuck and configured to rotate with the drill chuck, and wherein the surgical drill bit comprises a drilling portion for drilling through bone, the drilling portion extending distally along the drill bit axis from the shank portion to the distal end of the surgical drill bit, and wherein the drilling portion comprises a distal cutting region adjacent the distal end of the surgical drill bit and a fluted region disposed between the shank portion and the distal cutting region, and wherein the first outlet is defined in the distal cutting region and the second outlet is defined in the fluted region.

XXXV. The surgical drilling system of clause XXXIV, wherein the drilling portion of the surgical drill bit tapers toward the drill bit axis from the shank portion of the surgical drill bit to the distal end of the surgical drill bit.

XXXVI. The surgical drilling system of any one of clauses XXXII to XXXV, wherein the first and second characteristics of the fluid being transferred to the first and second inner channels of the surgical drill bit comprise one or more characteristics selected from a fluid velocity, a fluid volumetric flow rate, and a fluid pressure.

XXXVII. The surgical drilling system of any one of clauses XXXII to XXXVI, wherein the characteristic of the drilling medium at the first and second outlets of the surgical drill bit comprise one characteristic selected from a tissue presence and a tissue type.

XXXVIII. The surgical drilling system of any one of clauses XXXII to XXXVII, wherein the controller is configured to receive the first and second signals from the sensor and determine a breakthrough event has occurred based on the first and second signals from the sensor.

XXXIX. The surgical drilling system of clause XXXVIII, wherein the breakthrough event comprises one event selected from the surgical drill bit breaching through the bone and the surgical drill bit transitioning from a first bone structure to a second bone structure.

XL. The surgical drilling system of any one of clauses XXXVIII to XXXIX, wherein the controller is configured to arrest the drill chuck to stop the surgical drill bit from rotating responsive to the controller determining a breakthrough event has occurred.

XLI. The surgical drilling system of any one of clauses XXXVIII to XL, further comprising a robot arm coupled to the drill chuck configured to axially move the drill chuck and the surgical drill bit along the drill bit axis, wherein the controller is configured to arrest the robot arm from axially moving responsive to the controller determining a breakthrough event has occurred.

XLII. The surgical drilling system of any one of clauses XXXII to XLI, wherein the controller is configured to determine a position of the surgical drill bit in the bone based on one or both the first and second signals from the sensor.

The invention claimed is:

1. A surgical drilling system configured for bone drilling and configured to determine a characteristic of a drilling medium from a characteristic of fluid flow, said surgical drilling system comprising:
a drill chuck configured to be rotated by a motor;
a surgical drill bit configured to be coupled to the drill chuck, the surgical drill bit comprising:
a shank portion extending distally along a drill bit axis from a proximal end, the shank portion configured to be coupled to and rotated by the drill chuck, and the shank portion having a proximal surface defining a proximal opening, and
a drilling portion for drilling through bone, the drilling portion extending distally along the drill bit axis from the shank portion to a distal end, the drilling portion having a distal cutting region comprising:
a rake surface for cutting into a bone while drilling,
a clearance surface for directing bone chips away form the bone during drilling, and
a flank surface disposed between the rake surface and the clearance surface, the flank surface defining a distal opening, and the flank surface configured to abut the bone such that the distal opening is occluded by the bone while the rake surface is cutting into the bone,
wherein the shank and drilling portions collectively define an inner channel in fluid communication with the proximal and distal openings, and wherein the distal opening is configured to be occluded by the bone during drilling to establish fluid pressure within the inner channel;
a pump configured to transfer fluid from a fluid source into the inner channel of the surgical drill bit through the proximal opening of the surgical drill bit;
a sensor disposed in fluid communication with the inner channel and configured to generate a signal responsive to a characteristic of the fluid being transferred to the inner channel of the surgical drill bit; and
a controller configured to receive the signal form the sensor and determine a characteristic of the drilling medium at the distal opening of the surgical drill bit based on the signal, and wherein the controller is configured to arrest the drill chuck to stop the surgical drill bit from rotating responsive to the controller determining a breakthrough event has occurred.

2. The surgical drilling system of claim 1, wherein the flank surface of the surgical drill bit is generally planar and perpendicular to the drill bit axis.

3. The surgical drilling system of claim 1, wherein the drilling portion of the surgical drill bit further comprises a fluted region extending proximally toward the shank portion from the distal cutting region.

4. The surgical drilling system of claim 1, wherein the drilling portion of the surgical drill bit tapers toward the drill bit axis from the shank portion of the surgical drill bit to the distal end of the surgical drill bit.

5. The surgical drilling system of claim 1, wherein the distal opening of the surgical drill bit is offset from the drill bit axis.

6. The surgical drilling system of claim 1, wherein the characteristic of the fluid being transferred to the inner channel of the surgical drill bit comprises one or more characteristics selected from a fluid velocity, a fluid volumetric flow rate, and a fluid pressure, and wherein the characteristic of the drilling medium at the distal opening of the surgical drill bit comprises one characteristic selected from a tissue presence and a tissue type.

7. The surgical drilling system of claim 1, wherein the controller is configured to receive the signal from the sensor and determine a breakthrough event has occurred based on the signal from the sensor, and wherein the breakthrough event comprises one event selected from the surgical drill bit breaching through the bone and the surgical drill bit transitioning from a first bone structure to a second bone structure.

8. The surgical drilling system of claim 1, wherein the controller is configured to determine a position of the surgical drill bit in the bone based on the signal from the sensor.

9. A surgical drilling system configured for bone drilling and configured to determine a characteristic of a drilling medium from a characteristic of fluid flow, said surgical drilling system comprising:
a drill chuck configured to be rotated by a motor;
a surgical drill bit extending from a proximal end to a distal end along a drill bit axis, and the surgical drill bit configured to be coupled to the drill chuck and configured to rotate with the drill chuck, and the surgical drill bit comprising:
a shank portion adjacent the proximal end of the surgical drill bit, the shank portion configured to be coupled to and rotated by the drill chuck, and the shank portion having a proximal surface defining a proximal opening, and
a drilling portion for drilling through bone, the drilling portion extending distally along the drill bit axis form the shank portion to the distal end of the surgical drill bit, the drilling portion comprising:
a distal cutting region adjacent the distal end of the surgical drill bit for plunging into the bone, and
a fluted region disposed between the shank portion and the distal cutting region, the fluted region comprising a lateral surface defining a lateral opening,
wherein the shank and drilling portions collectively define an inner channel in fluid communication with the proximal and lateral openings, and wherein the lateral opening is configured to be occluded by the bone during drilling to establish fluid pressure within the inner channel;
a pump configured to transfer fluid form a fluid source into the inner channel of the surgical drill bit through the proximal opening of the surgical drill bit;
a sensor disposed in fluid communication with the inner channel and configured to generate a signal responsive to a characteristic of the fluid being transferred to the inner channel of the surgical drill bit; and
a controller configured to receive the signal from the sensor and determine a characteristic of the drilling medium at the lateral opening of the surgical drill bit based on the signal, and wherein the controller is configured to arrest the drill chuck to stop the surgical drill bit from rotating responsive to the controller determining a breakthrough event has occurred.

10. The surgical drilling system of claim 9, wherein the drilling portion of the surgical drill bit tapers toward the drill bit axis from the shank portion of the surgical drill bit to the distal end of the surgical drill bit.

11. The surgical drilling system of claim 9, wherein the characteristic of the fluid being transferred to the inner channel of the surgical drill bit comprises one or more characteristics selected from a fluid velocity, a fluid volumetric flow rate, and a fluid pressure, and wherein the characteristic of the drilling medium at the lateral opening of the surgical drill bit comprises one characteristic selected from a tissue presence and a tissue type.

12. The surgical drilling system of claim 9, wherein the controller is configured to receive the signal from the sensor and determine a breakthrough event has occurred based on the signal from the sensor, and wherein the breakthrough event comprises one event selected from the surgical drill bit breaching through the bone and the surgical drill bit transitioning from a first bone structure to a second bone structure.

13. The surgical drilling system of claim 9, further comprising a robot arm coupled to the drill chuck configured to axially move the drill chuck and the surgical drill bit along the drill bit axis, wherein the controller is configured to arrest the robot arm from axially moving responsive to the controller determining a breakthrough event has occurred.

14. The surgical drilling system of claim 9, wherein the controller is configured to determine a position of the surgical drill bit in the bone based on the signal from the sensor.

15. The surgical drilling system of claim 9, wherein the fluted region comprises two lands extending between the shank portion and the distal cutting region, and wherein the two lands define a flute between the two lands.

16. The surgical drilling system of claim 15, wherein one of the two lands comprises the lateral surface that defines the lateral opening, and wherein the lateral surface faces away from the flute.

17. The surgical drilling system of claim 9, wherein the distal cutting region of the surgical drill bit is free of an opening in fluid communication with the inner channel.

* * * * *